United States Patent [19]

Buess et al.

[11] Patent Number: 5,365,171
[45] Date of Patent: Nov. 15, 1994

[54] REMOVING THE EFFECTS OF ACOUSTIC RINGING AND REDUCING TEMPERATURE EFFECTS IN THE DETECTION OF EXPLOSIVES BY NQR

[75] Inventors: Michael L. Buess, Alexandria, Va.; Allen N. Garroway; James P. Yesinowski, both of Fort Washington, Md.

[73] Assignee: The United States of America as represented by the Secretary of the Navy, Washington, D.C.

[21] Appl. No.: 983,990
[22] Filed: Nov. 30, 1992
[51] Int. Cl.$^5$ .................................. G01R 33/20
[52] U.S. Cl. .................................. 324/307; 324/300
[58] Field of Search ............. 324/300, 307, 308, 309, 324/310, 311, 312, 313, 314, 318, 322

[56] References Cited

U.S. PATENT DOCUMENTS

| | | | |
|---|---|---|---|
| 4,438,400 | 3/1984 | Patt | 324/312 |
| 4,887,034 | 12/1989 | Smith | 324/307 |
| 5,023,551 | 6/1991 | Kleinberg et al. | 324/303 |
| 5,026,942 | 6/1991 | Fellmann et al. | 585/467 |
| 5,159,617 | 10/1992 | King et al. | 324/307 |
| 5,168,224 | 12/1992 | Maruizumi et al. | 324/300 |
| 5,206,592 | 4/1993 | Buess et al. | 324/307 |
| 5,233,300 | 8/1993 | Buess et al. | 324/307 |

FOREIGN PATENT DOCUMENTS 2254923A  10/1992  United Kingdom .

OTHER PUBLICATIONS

Buess et al., Acoustic Ringing Effects in Pulsed Nuclear Magnetic Resonance Probes, Rev. Sci. Instrum. 49(8), Aug. 1978, pp. 1151–1155.
Fukushima et al., "Spurious Ringing in Pulse NMR," Journ. of Magnetic Resonance, 33, 199–203 (1979).
Gerothanassis, "Method of Avoiding the Effects of Acoustic Ringing in Pulsed Fourier Transform Nuclear Magnetic Resonance Spectroscopy," Progress in NMR Spectroscopy, vol. 19, pp. 267–329, 1987.
Peterson et al., "N Nuclear Quadrupole Resonance and Relaxation Measurements of Sodium Nitrite," The Journ. of Chemical Physics, vol. 64, No. 2, 15 Jan 1976.
Karpowicz et al., "Librational Motion of Hexahydro-1,3,5-Trinitro-s-Triazine Based on the Temperature Dependence of the Nitrogen-14 Nuclear Quadrupole Resonance Spectra: The Relationship to Condensed-Phase Thermal Decomposition," J. Phys. Chem. 1983, 87, pp. 2109–2112.
Carr, "Steady-State Free Precession in Nuclear Magnetic Resonance," Physical Review, vol. 112, No. 5, 1958, pp. 1701.
Ernest et al., "Application of Fourier Transform Spectroscopy to Magnetic Resonance," The Review of Scientific Instruments, vol. 37, No. 1, 1966, pp. 93–102.
Hinshaw, "Image Formation by Nuclear Magnetic Resonance: The Sensitive–Point Method," J. of Applied Phys., vol. 47, No. 8, 1976, pp. 3709–3721.
Gyngell, "The Steady–State Signals in Short–Repetition–Time Sequences," J. of Magnetic Resonance 81, 474–483, 1989.

*Primary Examiner*—Michael J. Tokar
*Attorney, Agent, or Firm*—Thomas E. McDonnell; Barry A. Edelberg

[57] ABSTRACT

Acoustic ringing and adverse effects from variations in the NQR detection of explosives and narcotics are minimized or eliminated. A specimen is irradiated with a modified steady state steady state free precession (SSFP) pulse sequence which combines a phase-alternated pulse sequence (PAPS) with a non-phase-alternated pulse sequence (NPAPS). The resulting signals from the PAPS and NPAS may then be coadded to cancel out the FID contributions to the signals. By canceling out the FID contributions to the signals, the effects of probe ringing and other extraneous responses, as well as the effect of temperature variation, are minimized or removed. The present method is especially effective in the detection of explosives and narcotics having $^{14}N$ or $^{35,37}Cl$ nuclei. A steady state free precession pulse which is especially useful with the method of the present invention is the strong off-resonance comb (SORC). In another embodiment of the invention, the effects of probe ringing can also be minimized or removed by repeating the detection procedure at a frequency which is sufficiently off-resonance so that only frequency independent effects, such as probe-ringing, can be observed.

14 Claims, 9 Drawing Sheets $\frac{1}{4} \times [A-B-C-D] =$

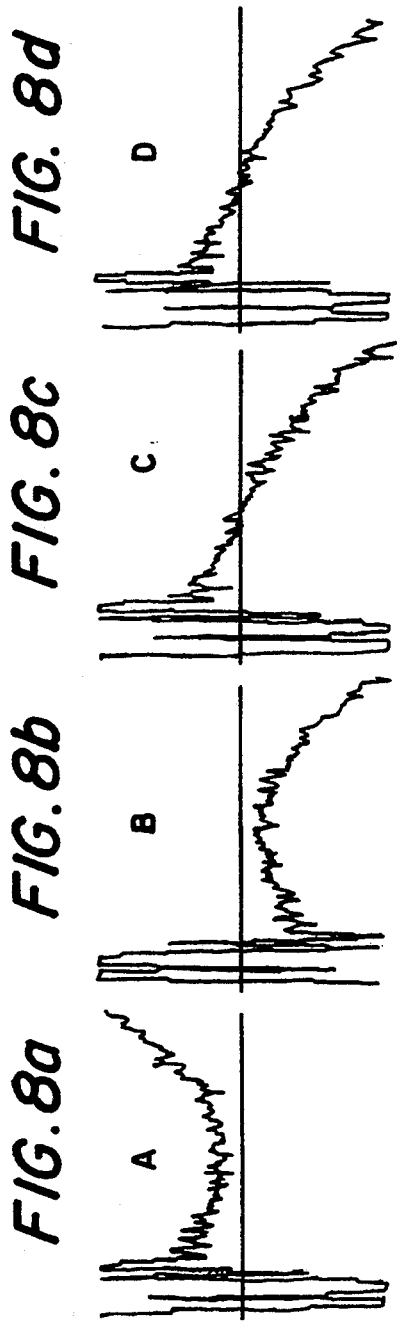

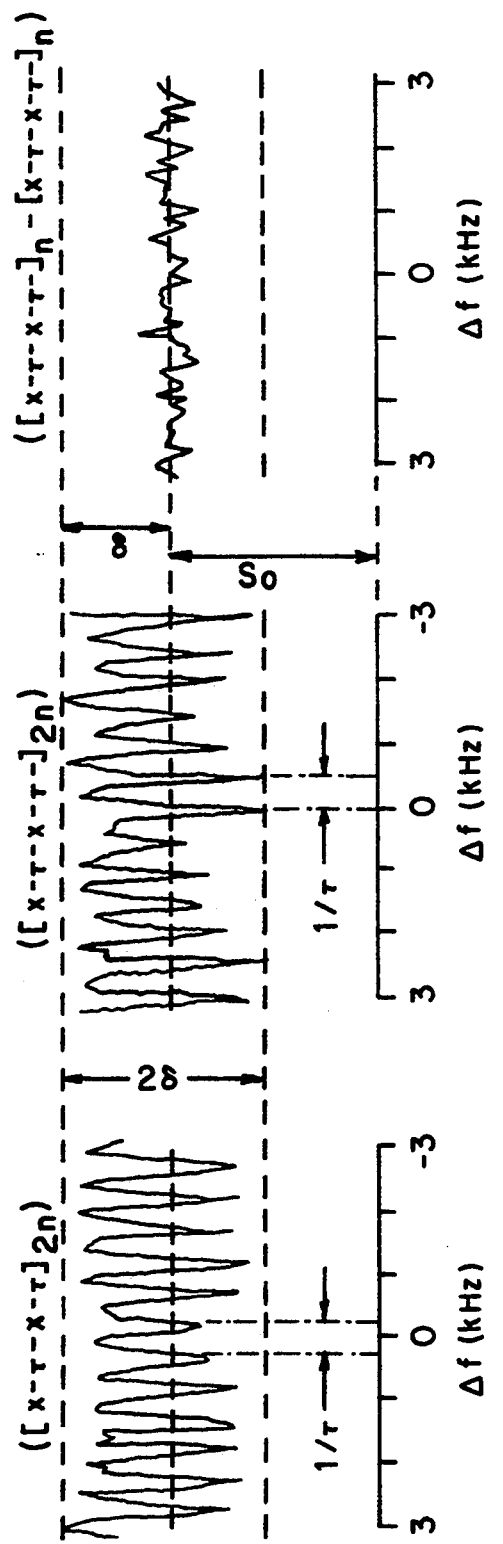

REMOVING THE EFFECTS OF ACOUSTIC RINGING AND REDUCING TEMPERATURE EFFECTS IN THE DETECTION OF EXPLOSIVES BY NQR

BACKGROUND OF THE INVENTION

1. Field of the Invention

The present invention relates generally to nuclear quadrupole resonance (NQR) and more specifically to the detection of explosives and narcotics by nuclear quadrupole resonance.

2. Description of the Background Art

As described in U.S. Ser. No. 07/704,744, filed May 23, 1991, now U.S. Pat. No. 5,206,592 and in U.S. Ser. No. 07/730,772, filed Jul. 16, 1991, now U.S. Pat. No. 5,238,234 both of which are incorporated herein by reference, NQR can be an effective means of detecting explosives and narcotics. In particular, NQR is useful in the detection of nitrogenous or chlorine-containing explosives and narcotics (or, more generally, materials containing quadrupolar nuclei such as $^{14}N$, $^{35,37}Cl$, etc), such as carried in luggage, mail, small cargo or on a person. This general NQR approach is referred to as 'pure' NQR to indicate that no externally applied static magnetic field is required.

Unfortunately, the radiofrequency (RF) pulses used in the typical NQR explosives and narcotics detection sequences will induce an acoustic ringing in certain items, typically magnetized iron or ceramic, which may occasionally be found in baggage. This ringing may last on the order of a millisecond and be comparable in size to the NQR signal amplitude corresponding to a threat quantity of explosives.

If this acoustic ringing were not removed, then one could suffer an increased false alarm rate (false positive) for those bags containing such materials. Alternatively, a low false alarm rate could be achieved by increasing substantially the threshold 'alarm' setting, but at the expense of increasing the minimum detectable quantity.

Acoustic ringing (sometimes called magnetoacoustic ringing or probe ringing) is a well-known, though not completely well-understood, phenomenon in conventional NMR, where an external, static magnetic field is used. The basic mechanism is that the RF pulse induces eddy currents in a conductor. In a magnetic field, a force acts on these currents and hence on the conductor, inducing acoustical energy that bounces back and forth within the conductor. This pulse of acoustic energy correspondingly alters the magnetic coupling to the receiver coil, inducing a 'signal' that is in phase with the driving RF pulse and that persists until the acoustic energy is dissipated in the system.

Since there is no static magnetic field in pure NQR, the acoustic ringing mechanism is different than for NMR applications. A likely explanation is that the ferromagnetic domains in magnetized materials try to realign in response to the applied RF magnetic field. These (partial) realignments cause lattice distortions generating acoustic energy that then reflects back and forth within the sample.

For concreteness the present invention disclosure considers the elimination of acoustic ringing, though it will be appreciated that other mechanisms that contribute to extraneous probe ringing are also amenable to elimination according to the approach described herein.

In the related art of nuclear magnetic resonance (NMR), there are a number of approaches to reducing or removing extraneous probe ringing. Since the ringing is generally in the probe body or RF coil, rather than the specimen under study, mechanically redesigning the probe to employ materials that rapidly damp the acoustic wave is a viable option in NMR.

There are also a number of NMR pulse sequences that have proven effective in largely eliminating the effects of acoustic ringing. Such sequences generally rely upon the ability to invert the sign of the NMR signal in the rotating reference frame, but not that of the acoustic ringing signal in the same frame (or vice-versa). Thus, provided the offending acoustic ringing signal is reproducible over time, one can arrange to alternatively add and subtract the incoming signal so that the desired NMR signal is consistently added (in effect), while the acoustic signal alternately adds and subtracts to zero. As will be shown below, the cancellation techniques conventionally used for NMR are not directly applicable to NQR.

To remove the acoustic ringing in NMR, a second, well-known approach is to rely on the ability to invert (change the sign of) NMR magnetization by a conventional 180° or $\pi$ pulse. One possible sequence consists of a $\pi/2$ excitation pulse that produces, say, a positive NMR signal and a positive acoustic ringing signature. After magnetization is regenerated in a time $T_1$, the spin-lattice relaxation time, a $\pi$ inverting pulse is applied, followed a time $t_d$ later by a $\pi/2$ pulse. All pulses have the same phase. Provided $t_d$ is much less than $T_1$, the NMR signal will be inverted. Also, provided $t_d$ is long compared to the acoustic ringing signal, the acoustic signal will be the same as it was after the initial $\pi/2$ pulse. Addition and subtraction of the resulting signals removes the component of acoustic ringing, while preserving the NMR signal.

However, for the general NQR case, these simple strategies presented above are not appropriate. In the detection of explosives or narcotics in a package or on a person by NQR, the acoustic ringing arises from magnetized components within the specimen, e.g. a suitcase or package. Identifying and then removing the offending contents is not a desirable solution. Furthermore, the straightforward sequence discussed above for NMR does not work for NQR. For a polycrystalline specimen, it is well-known that there is no RF pulse that inverts the entire NQR 'magnetization'.

Additionally, it is well-known that the exact NQR resonance frequency varies with temperature. Obviously, this temperature variation has some undesirable effects in NQR detection schemes. While conventional schemes to minimize these undesirable effects exist, the method of the present invention can effectively remove both probe ringing and minimize temperature effects.

SUMMARY OF THE INVENTION

Accordingly, it is an object of this invention to enhance the effectiveness of NQR as means of detecting explosives and narcotics.

It is another object of the present invention to reduce or eliminate false positives in the detection of explosives and narcotics by NQR.

It is a further object of the present invention to reduce interference, in the NQR detection of explosives and narcotics, cause by extraneous probe ringing.

It is a yet further object of the present invention to minimize temperature effects in NQR.

These and additional objects of the invention are accomplished by an NQR scheme in which a specimen is irradiated with a modified steady state free precession (SSFP) pulse sequence that combines a phase-alternated pulse sequence (PAPS) with a non-phase-alternated pulse sequence (NPAPS). By appropriately coadding the signals in the PAPS and NPAPS portions of the modified sequence, one can remove either the FID or the echo contribution to the NQR signal while retaining the other. A coaddition procedure that removes the FID contribution also cancels out extraneous responses, such as magnetoacoustic ringing, having phase and amplitude that are determined only by the preceding pulse. This coaddition procedure also minimizes the effect of temperature variation upon the NQR signal.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein:

FIGS. 8a through 8e show the results of the modified sequence under conditions identical to those in FIGS. 7a through 7e, except that a 2 g rare earth magnet was placed in the RF coil along with the cocaine base sample.

FIGS. 9a through 9c shows the resonance offset dependence of the magnitude of the NQR signal intensity of the 4.645 MHz line of sodium nitrite using three versions of the SSFP RF pulse sequence.

DESCRIPTION OF THE PREFERRED EMBODIMENTS

1. Exemplary Methods and Apparatuses With Which the Present Invention May Be Used.

Before the present invention is described, a general discussion of NQR detection of explosives, including prior useful improvements therein, is helpful to assure complete disclosure of a preferred embodiment for using the invention. While this discussion will concentrate on specific apparatuses and methods useful with the present invention, it should be understood that the present invention may be effectively used with many other NQR methods and apparatuses.

Figure 1:
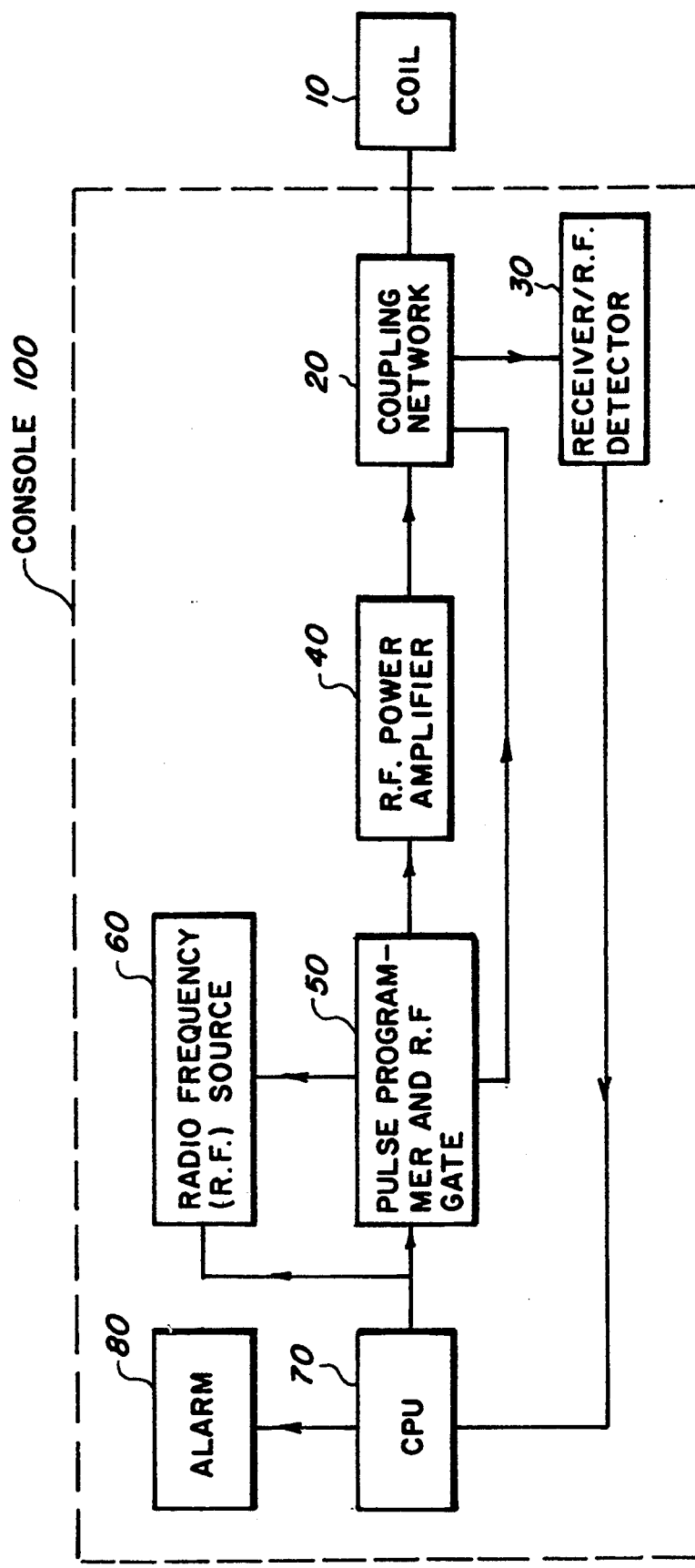
FIG. 1 illustrates a block diagram of the NQR system for the present invention.

FIG. 1 illustrates a block diagram for the NQR detection system for an embodiment of the present invention. A radio frequency source 60, a pulse programmer and RF gate 50 and an RF power amplifier 40 are provided to generate a train of radio frequency pulses having a predetermined frequency to be applied to a coil 10. A coupling network 20 conveys the train of radio frequency pulses from the radio frequency source 60, the pulse programmer and RF gate 50 and the RF power amplifier 40 to the coil 10. The coupling network 20 also conducts the signal to the receiver/RF detector 30 from the coil 10 after a specimen is irradiated with the train of radio frequency pulses. A central processing unit (CPU) 70 controls the radio frequency source 60 and the pulse programmer and RF gate 50 to a predetermined frequency which coincides with or is near to a $^{14}$N, $^{35,37}$Cl, etc., NQR frequency of the type of explosive (e.g. all RDX-based explosives) or narcotic desired to be detected. The CPU 70 also compares the total (i.e., "integragated") nitrogen signal (or, more generally, the total signal from the quadrupolar nucleus of interest) with a predetermined threshold value. When the predetermined threshold value is exceeded, an alarm 80 is activated in response to the comparison by the CPU 70. The coupling network 20, the receiver/RF detector 30, the RF power amplifier 40, the pulse programmer and RF gate 50, the radio frequency source 60, the CPU 70 and the alarm 80 may be contained in a console 100 with only the coil 10 being outside of the console 100.

Figure 2A:
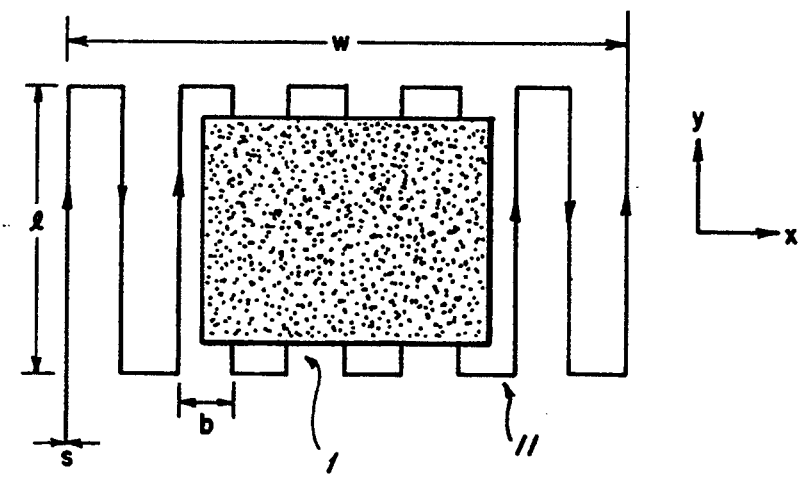
FIGS. 2A and 2B illustrate top and side views of a meanderline surface coil for an embodiment of the present invention with respect to a sample.
Figure 2B:
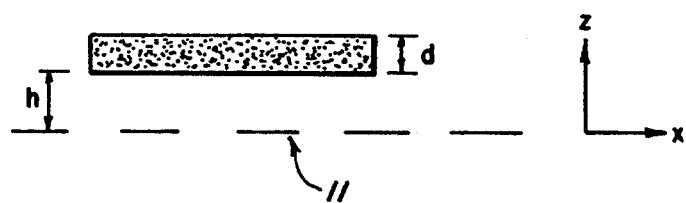

FIGS. 2A and 2B further illustrate the coil 10 as a meanderline surface coil 11 having a width w and a length l for detecting $^{14}$N pure NQR signals of a sample 1. The meanderline surface coil 11 is constructed of a serpentine array of parallel conductors being separated by a predetermined distance b. The conductor strips can theoretically be regarded as infinitely thin but having a finite width of s. FIG. 2B illustrates the sample 1, that has a thickness of d, being a height h above the surface of the meanderline surface coil 11.

In order to detect pure NQR signals from quadrupolar nuclei, it is necessary to use a coil producing an RF magnetic field that is confined as much as possible to the region of interest. The magnetic field in planes parallel to the surface of the meanderline surface coil 11 has a periodicity of the meanderline spacing b and the strength of the magnetic field drops off approximately as exp $(-\pi h/b)$, so that the effective RF magnetic field is confined to a region adjacent to the meanderline surface coil 11 with a penetration depth determined by the spacing b between the parallel conductors and not the overall size of the coil. As a result, the meanderline surface coil 11 is optimally suited for probing a sizable surface area to a limited depth. By contrast, the penetration depth of a more conventional circular surface coil is determined by the coil radius: making the circular surface coil larger increases the penetration depth.

The excitation and detection performed by the coil 10 utilizes a pure nuclear quadrupole resonance procedure performed in zero magnetic field so that no magnet is required. In the preferred embodiment, a meanderline surface coil 11 as illustrated in FIGS. 2A and 2B is used. However, for certain specific geometries other coils may be quite suitable: for example, a conventional solenoid, rectangular solenoid, Helmholtz, or toroidal coil may be used. The specimen 1 is irradiated with a train of radio frequency pulses developed by the RF power amplifier 40, the pulse programmer and RF gate 50, the radio frequency source 60 and the CPU 70 to have a frequency near to the $^{14}$N, $^{35,37}$Cl, etc. NQR frequency of the type of explosive or narcotic desired to be detected. For example, RDX has NQR resonance lines near 1.8, 3.4 and 5.2 MHz and PETN has resonance lines near 0.4, 0.5 and 0.9 MHz. Hence all RDX-types of explosive would be detected by examination near to 1.8, 3.4 or 5.2 MHz.

In a preferred embodiment, the train of radio frequency pulses is a steady state free precession (SSFP) pulse sequence. SSFP sequences were first introduced to NMR in 1958 by Carr, "Steady State Free Precession in Nuclear Magnetic Resonance," Phys. Rev. 112, 1693–1701 (1958), and have been developed and analyzed further for NMR (R. R. Ernst and W. A. Anderson, "Application of Fourier Transform Spectroscopy to Magnetic Resonance," Rev. Sci. Instrum. 37, 93–102 (1966); W. S. Hinshaw, "Image Formation by Nuclear Magnetic Resonance: The Sensitive Point Method," J. Appl. Phys. 47 3709–3721 (1976); M. L. Gyngell, "The Steady-State Signals in Short-Repetition-Time-Sequences," J. Magn. Reson. 81 478–483 (1989)). The name refers to the steady state condition that occurs when a spin system is irradiated with a continuous train of RF pulses each separated by an interval $\tau$. During $\tau$, the nuclear spins freely precess.

A strong off-resonance comb (SORC) of rf pulses of identical phases, introduced, in NQR, by Marino (S. M. Klainer, T. B. Hirschfeld, and R. A. Marino, "Fourier Transform Nuclear Quadrupole Resonance Spectroscopy", in "Fourier, Hadamard, and Hilbert Transforms in Chemistry" A. G. Marshall, Ed.; Plenum Press: New York (1982)) is one example of a SSFP pulse sequence. For pulse separations $\tau$ less than the spin-spin relaxation time $T_2$, the size of the steady state response signal after every pulse is about $\frac{1}{2}$ of the equilibrium magnetization. For a particular geometry the RF pulses are approximately 50 microseconds long and are spaced approximately 1 millisecond apart. In approximately 5 seconds, for example, 5000 signals can be coadded in order to improve the signal-to-noise ratio when compared to a single pulse or to a conventional data taking approach which requires a delay approximately equal to the spin-lattice relaxation time $T_1$. Because $T_1$ for $^{14}N$ is typically on the order of seconds, the improvement in the signal-to-noise ratio obtained in a given amount of time by using the SORC sequence is $(T_1/\tau)^{\frac{1}{2}}$, or a factor of approximately 30 in this example.

After applying the train of radio frequency pulses to the coil 10, the total nitrogen signal from the coil passes through a receiver/RF detector 30 and is sent to the CPU 70. The total nitrogen signal is compared to a predetermined threshold value and the alarm 80 is activated when the total nitrogen signal exceeds the predetermined threshold value.

Conventionally, intense rf magnetic fields are used to excite the NQR lines, and generation of such intense fields requires substantial rf power with the associated possibility of depositing unacceptable amounts of power into the scanned objects. Power deposition can have unfortunate consequences for scanning of baggage and small cargo, wherein at some suitably high power level, damage to electronics may occur by over voltage or local heating through electrostatic coupling of the electric field or inductive coupling to the magnetic field. For scanning people, rf power deposition, primarily by eddy current loss, can pose a problem at these frequencies (1–5 MHz). A detailed discussion of the effects of rf power and field strength values on articles and persons and the acceptable levels of exposure to rf energy is unnecessary here and beyond the scope of this disclosure.

An rf field strength of $B_1$ applied near the resonance frequency nutates the spins (for a spin I=1 nucleus) through an angle of $2\gamma B_1 t_w$, where $\gamma$ is the magnetogyric ratio of the nuclear spin and $t_w$ is the pulse width. For a fixed nutation angle, an intense pulse has a shorter duration and, correspondingly, excites a broader region of the spectrum. Conventionally, one excites the NQR resonance with a pulse sufficiently long to cause the spins to nutate through about 119°, giving a maximum magnetization. On commercial NQR spectrometers in a laboratory setting, the pulses required to obtain a 119° tip angle typically have widths of 20–50 $\mu s$ and cover a bandwidth $1/t_w$ of 50–20 kHz. The rf field strength $B_1$ used in such cases is therefore 10–25 gauss.

In the invention described in the above-mentioned U.S. Ser. No. 07/730,722, it was recognized that the magnitude of the rf field strength need only be larger or equal to the magnitude of the local magnetic field strength due to dipole-dipole contributions. Hence the necessary rf field strength $B_{1min}$ is of the order of $1/\gamma T_2$, where $T_2$ is the spin-spin relaxation time due to dipolar coupling. Therefore, for example, the strong off resonance comb excitation will work quite satisfactorily at such low rf intensity. For RDX-based explosives, the present invention has successfully utilized rf fields as low as 0.7 G (0.07 mT). (The width of the $^{14}N$ NQR line is also partly determined by inhomogeneous interactions due to a distribution of the quadrupolar coupling constants, induced by strain, impurities and variations in temperature. Such an inhomogeneous contribution to the width is not as important as the homogeneous contribution from the dipole-dipole coupling.)

Therefore, although the conventional techniques apply an rf field of a strength that is at least 100 times greater in magnitude than that of the local magnetic field, successful NQR detection of nitrogenous explosives and narcotics can be achieved by using a rf field strength to local field strength ratio of from 1 or about 1 to about 50, preferably as close as possible to 1. Typically, a ratio of about 2 to about 30, more typically a ratio of about 2 to about 20, and most typically a ratio of about 2 to about 10 is used.

In practice, suitcase-sized sample volumes can be inspected at rather modest peak and average rf power levels. Furthermore, this approach makes feasible the examination of people by large surface coils, such as the meanderline, or even 'volume' coils such as a solenoid.

Various coils may be used according to the present invention, although all may not work equally well. For example, a meanderline coil, a circular surface coil, a pancake coil, and other coils may be successfully used.

In an embodiment of the present invention, the coupling network 20, the receiver/RF detector 30, the RF power amplifier 40, the pulse programmer and RF gate 50, the radio frequency source 60, the CPU 70 and the alarm 80 are contained in a console 100 with the coil 10 attached thereto so that the scanner coil can be placed next to the specimen desired to be detected.

FIG. 2A indicates the direction of the current flow in the serpentine array. A current density $J_s(x)$ is related to the total current I as illustrated in the relationship of $$\int_0^{s/2} J_s(x)dx = \frac{1}{2}I. \quad [1]$$

Figure 3:
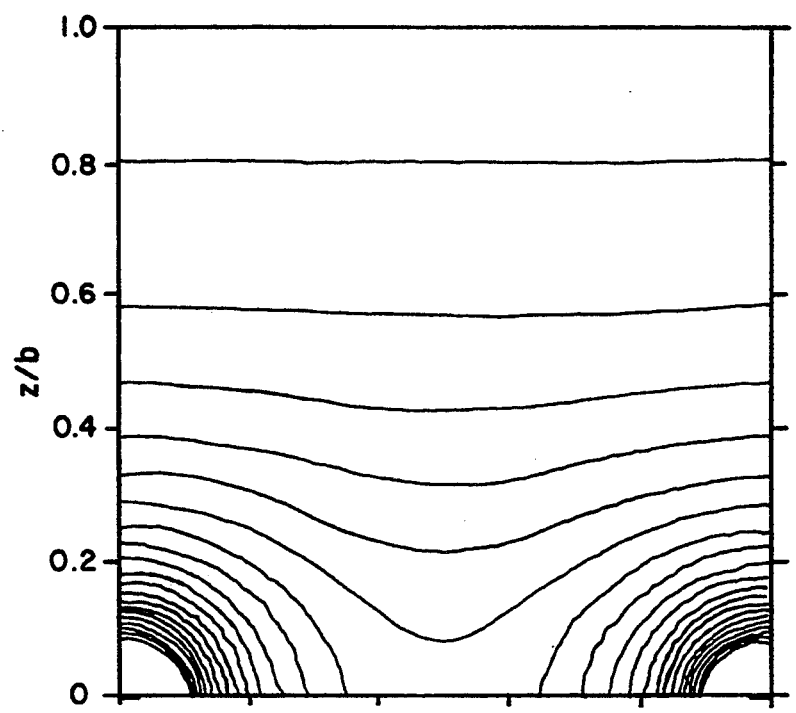
FIG. 3 illustrates the contour lines for the magnetic field strength of a meanderline surface coil in the XY plane.

By using magnetostatic boundary conditions, $J_s(x)$ between the conducting strips is 0 and $J_s(x)$ within the conducting strips corresponds to the relationship of $$J_s(x) = \frac{2\beta}{(2[\cos(2\pi x/b) - \cos(\pi s/b)])^{\frac{1}{2}}}, \quad [2]$$

where $\beta = \pi I[2bK(q)]^{-1}$ and $K(q)$ is the complete elliptic interval of the first kind with modulus $q = \sin(\pi s/2b)$. The resulting magnetic field components in the region of $z > 0$ and $B_y = 0$ are $$B_{\genfrac{}{}{0pt}{}{x}{z}} = \left(\genfrac{}{}{0pt}{}{-}{+}\right)\mu_0\beta \sum_{n=0}^{\infty} P_n[\cos(\pi s/b)]\exp[-(2n+1)\pi z/b] \times \left(\genfrac{}{}{0pt}{}{\cos}{\sin}\right)[(2n+1)\pi x/b], \quad [3]$$

where $P_n[\cos(\pi s/b)]$ is a Legendre polynomial of order n. In a thin layer sample adjacent to a meanderline surface coil, both the strength and direction of the RF magnetic field vary over the specimen according to equation [3]. An average must be taken at each location within the sample in order to obtain the NQR signal intensity. The quantity of interest in NQR detection is the magnitude of the RF field $B_1 = 2[B_x^2 + B_z^2]^{\frac{1}{2}}$. FIG. 3 illustrates the contour presentation of the magnetic field intensity from equation 3 and predicts the RF field profile. As illustrated in FIG. 3, the z component of the magnetic field reaches a maximum midway between the conducting strips and the modulus of the magnetic field is a maximum near the strip edges where $B_x$ is large, but the magnetic field never vanishes between the conducting strips due to the contribution of $B_z$.

Figure 4:
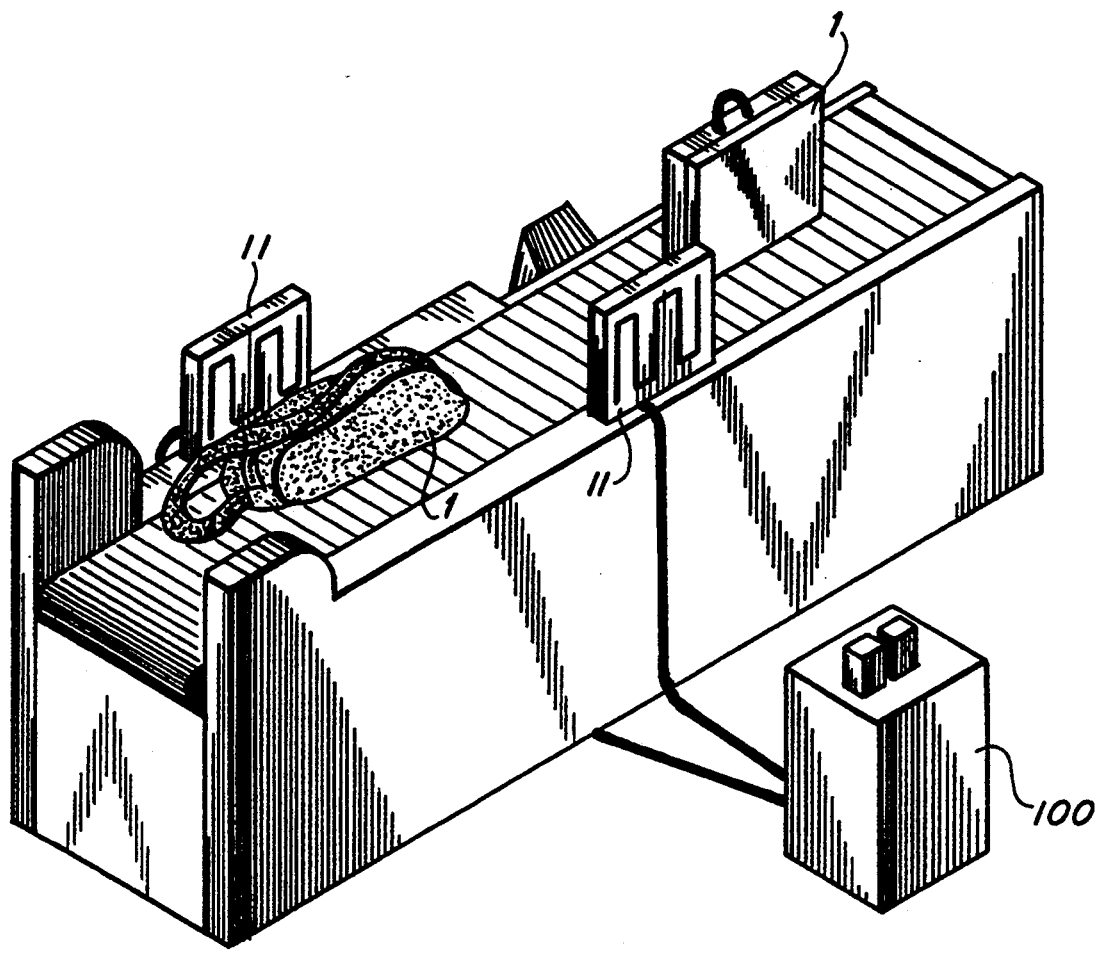
FIGS. 4 and 5 illustrate the implementation of the NQR detection system for the present invention.
Figure 5:
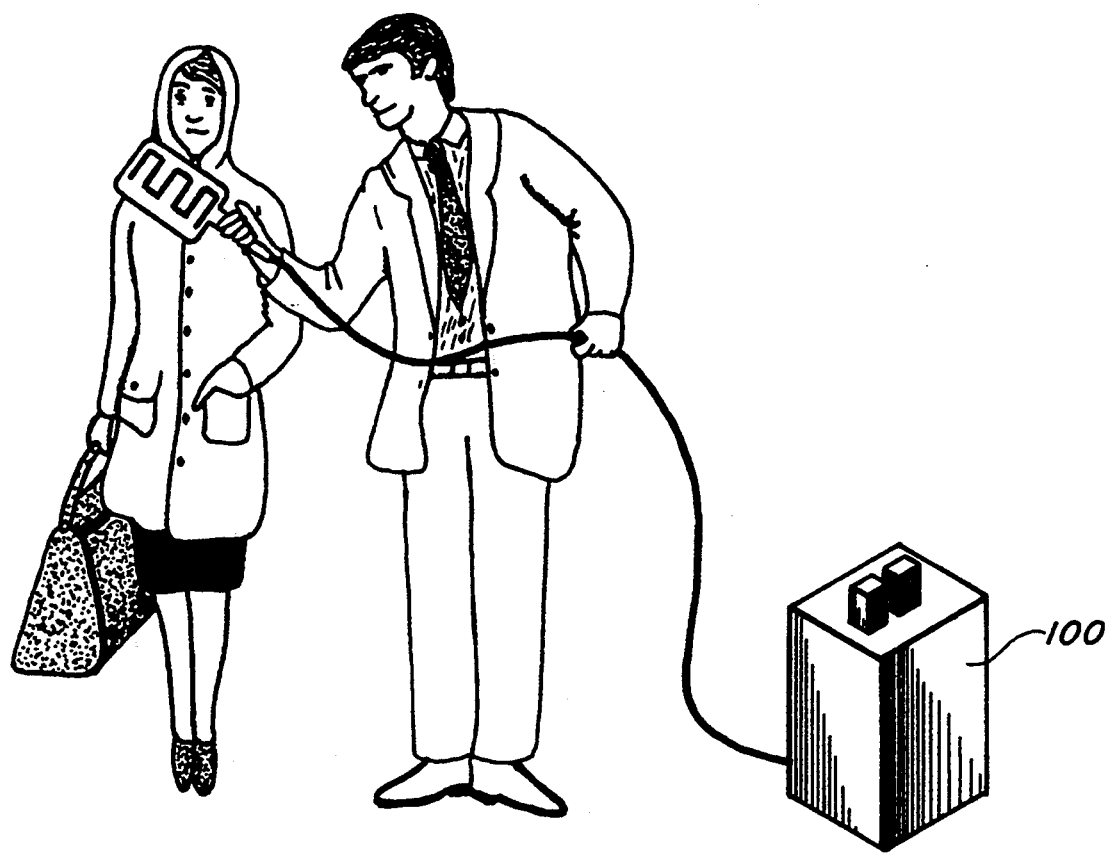

FIGS. 4 and 5 illustrate the possible use of such an NQR system for detecting explosives and narcotics in actual use. For clarity in FIG. 4 two meanderline inspection coils are shown quite far from the baggage to be inspected. In such an application, the geometry would be altered to bring the coils much closer to the bags. Alternatively, a large circular or rectangular solenoidal coil could be employed.

2. Characteristic aspects of the present invention

One embodiment of the present invention uses a modified version of the aforementioned SSFP pulse sequence. The success of this embodiment using the SSFP sequences relies on the fact that the magnetoacoustic ringing induced by an RF pulse is in phase with that pulse, whereas under the SSFP sequence, such as SORC, the NQR signal following a pulse has two contributions: the free induction decay (FID), which is in phase with that pulse, and the echo, which has a phase determined by both that pulse and the previous pulse. In this modified sequence the FID contributions cancel out along with any magnetoacoustic signals that are present, while the echo contributions to the NQR signal are left intact.

Figure 6:
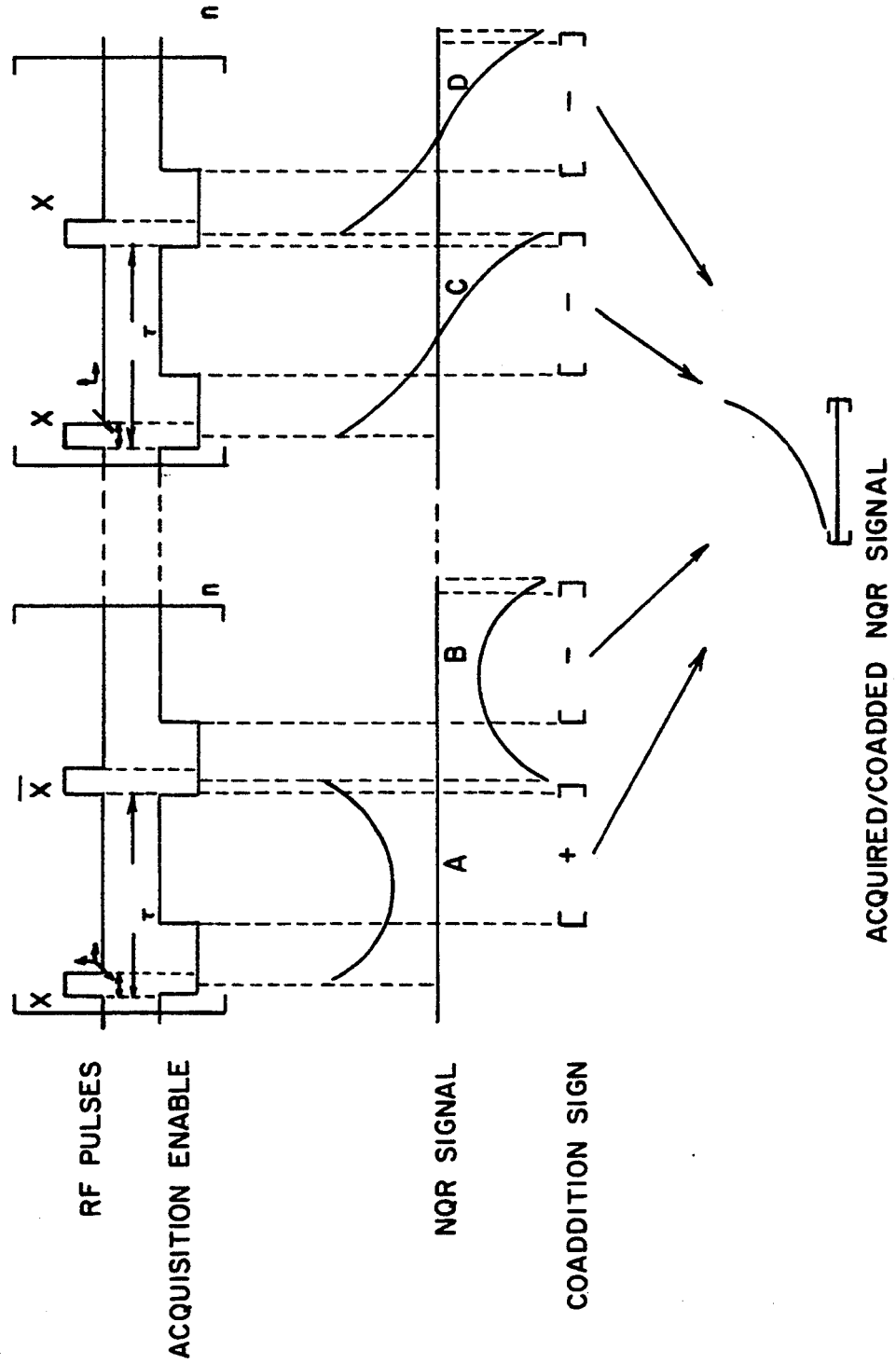
FIG. 6 is a timing diagram of the modified version of the SSFP sequence used to eliminate acoustical ringing.
Figures 7A, 7B, 7C, 7D:
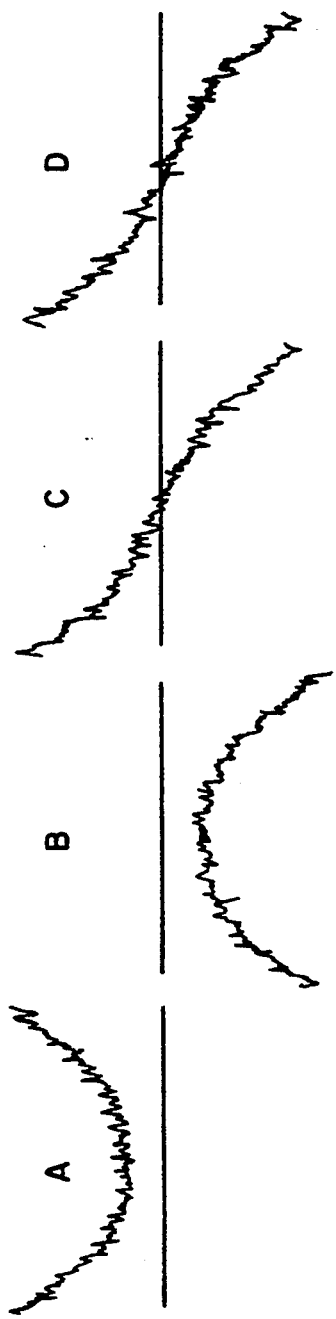
FIGS. 7a through 7e show the $^{14}$N NQR signal obtained at room temperature using this combined sequence (PAPS+NPAPS) at the 3.817 MHz resonance frequency of cocaine base (12.9 g) under the conditions $t_w=22$ $\mu$s, $\tau=5$ ms, and n=64.
Figure 7E:
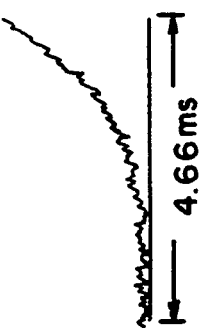

FIG. 6 is a timing diagram of the modified version of the SSFP sequence used in the present invention to eliminate acoustical ringing. In that figure x represents an RF pulse of duration $t_w$ and frequency equal to one of the NQR peaks of the explosive or narcotic to be detected, while $\bar{x}$ represents an RF pulse of the same duration and frequency as x, but of opposite RF phase. This modified sequence actually combines, in a temporally distinct manner, and in any order, two variations of SSFP pulse sequences: a phase-alternated pulse sequence (PAPS) or $[x-\tau-\bar{x}-\tau]_n$, and a non-phase-alternated pulse sequence (NPAPS) or $[x-\tau-x-\tau]_n$. (The NPAPS pulse train is identical to that of the original SORC sequence, the NPAPS nomenclature is introduced here to clearly distinguish the phase-alternated from the non-phase-alternated SSFP pulse trains.) The NPAPS and PAPS are applied during non-overlapping time intervals. The PAPS and NPAPS may be chained (i.e., successive), or a time lag may occur between the irradiation of the sample with the NPAPS and the irradiation of the sample with the PAPS. Typically, the NPAPS and PAPS sequences are chained to minimize the time required for detection. The NPAPS and PAPS may be applied to the specimen in any order. Additionally, while the NPAPS and PAPS are typically applied to the specimen over time intervals of the same length, the time interval during which the NPAPS is applied need not equal the time interval during which the PAPS is applied. If the NPAPS and PAPS are applied to the specimen for unequal amounts of time, the total NQR response to each signal will need to be weighted during the coaddition step to assure cancellation of the FID contribution to the response signal. Additionally, the PAPS and the NPAPS may each be generated by the same device, or, less preferably, by separate signal generators. Likewise, the PAPS and NPAPS may be applied to the specimen by the same coil, or, less preferably, by two distinct coils. Although FIG. 6 shows square pulses, other pulse shapes may be used.

As stated above, the NQR signal that occurs during the interval $\tau$ between pulses has two contributions: a free induction decay (FID) and an echo. As shown in FIG. 6, the sign, or relative phase, of the FID signal in both the PAPS (the simulated NQR signals labelled A and B) and NPAPS (C and D) portions of the modified sequence is determined only by the phase of the RF pulse that precedes it. However, the sign of the PAPS NQR echo signal is the same as that of the FID signal in the same interval, whereas the NPAPS FID and echo have opposite signs. Therefore, by appropriately coadding the signals in the PAPS and NPAPS portions of the modified sequence, one can remove either the FID or echo contributions to the NQR signal while retaining the other. The coaddition procedure indicated in FIG. 6 retains the echo contribution and removes the FID.

FIGS. 7a through 7e show the $^{14}$N NQR signal obtained at room temperature using this combined sequence (PAPS+NPAPS) at the 3.817 MHz resonance frequency of cocaine base (12.9 g) under the conditions $t_w = 22$ $\mu$s, $\tau = 5$ ms, and n = 64. The pulse sequence was repeated 512 times in order to increase the signal-to-noise ratio. Traces A–D are the actual NQR signals corresponding to the simulated NQR signals designated in the same manner in FIG. 6. The bottom trace in FIGS. 7a through 7e are the properly coadded sum of traces A–D and demonstrates the elimination of the FID signal.

Alternatively, by changing the coaddition sign of the NPAPS signal (C and D in FIG. 6) from minus to plus, one retains the FID while removing the echo contribution. However, the coaddition procedure indicated in FIG. 6 is preferred because it also cancels out extraneous responses, such as magnetoacoustic ringing, having phase and amplitude that are determined only by the preceding pulse.

FIGS. 8a through 8e show the results of the modified sequence under conditions identical to those in FIG. 7, except that a 2 g rare earth magnet was placed in the RF coil along with the cocaine base sample in order to provide a very large, extraneous signal from magnetoacoustic ringing. Notice that the strong acoustic ringing present at the beginning of traces A-D is absent in the properly coadded trace at the bottom FIGS. 8a through 8e.

There is still a final, less elegant approach that may be invoked if the cancellation of the acoustic ringing is not perfect. The NQR signal occurs only in a narrow frequency region while the acoustic ringing is essentially frequency independent, depending on the acoustic standing waves created in the specimen. Hence, repeating the NQR explosives detection procedure sufficiently far from resonance will give substantially the same acoustic signal, but no NQR signal. Any signal obtained from this far off-resonance detection procedure can then be subtracted from the NQR signal obtained in the detection procedure performed in the narrow frequency region of interest. Such a strategy can determine whether an alarm condition arose from acoustic ringing incompletely removed by the above pulse sequence.

The use of a modified SSFP sequence according to the present invention combined with coaddition of the response signals also minimizes the effects of temperature variations upon the signal. The full theory for the SSFP sequence for the $^{14}$N spin-1 NQR case has not been yet presented. However, the analogous SSFP sequences have been used for many years in NMR and are discussed phenomenologically for NQR by Klainer, supra. As discussed above, in the SSFP sequence the resulting NQR signal is a superposition of FID and echo contributions. In addition to its dependence on the phase of the RF pulses, the phase of the echo contribution also depends upon the amount of precession during the interval between RF pulses created by resonance offset. This resonance offset could arise from temperature effects. Hence, as a function of resonance offset, the echo and FID contributions will interfere constructively and destructively, with the actual degree of interference determined by the details of relaxation times $T_1$ and $T_2$ and the interpulse spacing. From the standpoint of explosives or narcotics detection, this interference phenomenon in the net signal results in a periodic variation in the detectability of the explosives or narcotics as a function of resonance offset and, hence, of temperature. Typically, this variation in detectability is about ±20%.

The aforementioned modification to the SSFP sequence removes the FID contribution to the NQR signal by appropriate choice of RF phases, so there is no longer an interference effect arising from resonance offsets due to temperature variation. This removal of the FID contribution to the NQR signal also removes acoustic ringing. FIGS. 9a through 9c shows the resonance offset dependence of the magnitude of the NQR signal intensity of the 4.645 MHz line of sodium nitrite using three versions of the SSFP RF pulse sequence. FIGS. 9a and 9b were obtained using the PAPS and NPAPS variations, respectively, while FIG. 9c was obtained by using the combined, or modified, version of FIG. 6. The total number of coadded transients was the same in all three cases. Note that all three versions of the SSFP sequence produce the same average signal intensity, $S_0$; however, the PAPS and NPAPS sequences produce NQR responses that vary periodically in $1/\tau$, whereas the response to the modified version is constant over the resonance offset range indicated in FIGS. 9a through 9c. In this case, the NQR signal obtained using the aforementioned modified version is approximately ⅔ of the maximum NQR signal obtainable with the PAPS or NPAPS versions. However, the lack of oscillations in the modified SSFP NQR signal intensity provides a greater tolerance for temperature-related shifts in the NQR frequency.

Significantly, an SSFP pulse sequence modified according to the present invention is also efficient in providing a usable signal-to-noise ratio. Other pulse sequence do not suffer from the interference of echo and FID contributions, but they are not as efficient in providing an adequate signal-to-noise ratio.

The coaddition steps described herein are performed digitally. The signals may be digitized and their values (with either a + or − sign) stored in a computer. Alternatively, a computer can coadd the numbers on the fly, so that only a running sum is maintained during the pulse sequence. Means for digitization and coaddition of data are well-known and need not be discussed in detail herein.

Obviously, many modifications and variations of the present invention are possible in light of the above teachings. It is therefore to be understood that, within the scope of the appended claims, the invention may be practiced otherwise than as specifically described.

What is claimed is:

1. A system for detecting a substance selected from the group consisting of explosives and narcotics in a specimen by nuclear quadrupole resonance, comprising:

pulse generating means for generating a set of radio frequency pulse sequences having a predetermined frequency, said set of radio frequency pulse sequences comprising:

a first steady state free precession RF pulse sequence and;

a second steady state free precession RF pulse sequence temporally distinct from said first RF pulse sequence;

wherein each pulse of said first RF pulse sequence is of the same phase, duration, pulse separation and frequency, each pulse of said second RF pulse sequence having the same duration, pulse separation and frequency as the pulses of said first pulse sequence, said pulses of said second RF pulse sequence being, alternately, of the same phase as those of said first pulse sequence and of the opposite phase as those of said first pulse sequence;

a coil means for irradiating the specimen with said set of radio frequency pulse sequences and detecting a total nuclear quadrupole resonance signal in response to irradiating the specimen, said total nuclear quadrupole resonance signals produced in response to said first RF pulse sequence and second RF pulse sequence each including a free induction decay contribution and an echo contribution;

coupling means for transmitting said set of radio frequency pulses to said coil means and receiving said total nuclear quadrupole resonance signal from said coil means;

means for adding the total nuclear quadrupole resonance signal produced in response to said first RF pulse sequence to the total nuclear quadrupole resonance signal produced in response to said second RF pulse sequence so that said free induction decay contributions to each of said total nuclear quadrupole resonance signals cancel and only the echo contributions to said total nuclear quadrupole resonance signal remain, thus providing a coadded signal;

comparing means for comparing said coadded signal to a predetermined threshold value; and an alarm for signaling when said coadded signal exceeds said predetermined threshold value.

2. A system according to claim 1, wherein said predetermined frequency of said set of RF pulse sequences are near to a $^{14}N$, $^{35}Cl$ or $^{37}Cl$ NQR frequency of said substance to be detected.

3. A system according to claim 2, wherein said substance to be detected comprises an explosive including a $^{14}N$ nucleus.

4. A system according to claim 1, wherein said pulse generating means comprises a radio frequency source, a pulse programmer, a radio frequency gate and a radio frequency power amplifier.

5. A method for detecting a substance, selected from the group consisting of explosives and narcotics, in a specimen by nuclear quadrupole resonance, comprising the steps of:

(a) generating a first steady state free precession RF pulse sequence having a predetermined frequency, each pulse of said first RF pulse sequence being of the same phase, duration, pulse separation and predetermined frequency;

(b) transmitting said first RF pulse sequence to a coil;

(c) irradiating the specimen in response to said RF pulse sequence transmitted to said coil at said step (b) during a first time interval;

(d) detecting a first total nuclear quadrupole resonance signal in response to irradiating the specimen at said step (c);

(e) receiving said first total nuclear quadrupole resonance signal detected at said step (d);

(f) generating a second steady state free precession RF pulse sequence, each pulse of said second RF pulse sequence having the same duration, pulse separation and frequency as the pulses of said first pulse sequence, said pulses of said second RF pulse sequence being, alternately, of the same phase as those of said first pulse sequence and of the opposite phase as those of said first pulse sequence;

(g) transmitting said second RF pulse sequence to a coil;

(h) irradiating the specimen in response to said second RF pulse sequence transmitted to said coil at said step (g) during a second time interval non-overlapping with said first time interval;

(i) detecting a second total nuclear quadrupole resonance signal in response to irradiating the specimen at said step (h);

(j) receiving said second total nuclear quadrupole resonance signal detected at said step (i);

(k) adding the total nuclear quadrupole resonance signal produced in response to said from said first RF pulse sequence to the total nuclear quadrupole resonance signal produced in response to said second RF pulse sequence so that said free induction decay contributions to each of said total nuclear quadrupole resonance signals cancel and only the echo contributions to said total nuclear quadrupole resonance signal remain, thus providing a coadded signal;

(l) comparing said coadded signal to a predetermined threshold value; and (m) signaling when said coadded signal exceeds said predetermined threshold value.

6. The method of claim 5, wherein said first and second time intervals are of about equal duration.

7. The method of claim 5, wherein said predetermined frequency of said set of RF pulse sequences are near to a $^{14}N$, $^{35}Cl$ or $^{37}Cl$ NQR frequency of said substance to be detected.

8. The method of claim 5, wherein said substance to be detected comprises a narcotic including a $^{14}N$ nucleus.

9. The method of claim 5, wherein said substance to be detected comprises an explosive including a $^{14}N$ nucleus.

10. A method for detecting a substance selected from the group consisting of explosives and narcotics, in a specimen by nuclear quadrupole resonance, comprising the steps of:

(a) generating a steady state free precession pulse sequence having a predetermined frequency;

(b) transmitting said steady state free precession pulse sequence to a coil;

(c) irradiating the specimen in response to said steady state free precession pulse sequence transmitted to said coil at said step (b);

(d) detecting a total nuclear quadrupole resonance signal in response to irradiating the specimen at said step (c);

(e) receiving said total nuclear quadrupole resonance signal detected at said step (d);

(f) repeating step (a) through (e) at a second frequency sufficiently off resonance from the nuclear quadrupolar resonance signal of a nucleus detectable at said first frequency that no nuclear quadrupolar resonance signal for said nucleus occurs at said second frequency;

(g) subtracting the total nuclear quadrupolar resonance signal obtained in step (f) from the total nuclear quadrupolar resonance signal obtained in step (e).

11. The method of claim 5, further comprising the steps of (1) generating a third steady state free precession pulse sequence having a second frequency sufficiently off-resonance from the nuclear quadrupolar resonance signal of a nucleus detectable at said predetermined frequency that no nuclear quadrupolar resonance signal for said nucleus occurs at said second frequency;

(2) transmitting said third steady state free precession pulse sequence to a coil;

(3) irradiating the specimen in response to said third steady state free precession pulse sequence transmitted to said coil at said step (2);

(4) detecting a third total nuclear quadrupole resonance signal in response to irradiating the specimen at said step (3);

(5) receiving said third total nuclear quadrupole resonance signal detected at said step (4);

(6) subtracting the third total nuclear quadrupolar resonance signal obtained in step (5) from the coadded signal obtained in step (k), the first nuclear quadrupole resonance signal obtained in step (e) or the second nuclear quadrupole resonance signal obtained in step (j).

12. The method of claim 11, wherein said predetermined frequency of said set of RF pulse sequences are near to a $^{14}N$, $^{35}Cl$ or $^{37}Cl$ NQR frequency of said substance to be detected.

13. The method of claim 12, wherein said substance to be detected comprises an explosive including a $^{14}N$ nucleus.

14. The method of claim 12, wherein said substance to be detected comprises a narcotic including a $^{14}N$ nucleus.

* * * * *